United States Patent
Lee et al.

(10) Patent No.: US 10,357,507 B2
(45) Date of Patent: *Jul. 23, 2019

(54) USE OF GINSENOSIDE M1 FOR INHIBITING RENAL FIBROSIS

(71) Applicant: Sheau-Long Lee, Taoyuan (TW)

(72) Inventors: Sheau-Long Lee, Taoyuan (TW); Yu-Chieh Lee, Taoyuan (TW); Ann Chen, Taipei (TW); Kuo-Feng Hua, Taiwan (CN); Shuk-Man Ka, Taipei (TW)

(73) Assignee: Sheau-Long Lee, Taoyuan (TW)

( * ) Notice: Subject to any disclaimer, the term of this patent is extended or adjusted under 35 U.S.C. 154(b) by 79 days.

This patent is subject to a terminal disclaimer.

(21) Appl. No.: 15/311,683

(22) PCT Filed: May 18, 2015

(86) PCT No.: PCT/CN2015/079156
§ 371 (c)(1),
(2) Date: Nov. 16, 2016

(87) PCT Pub. No.: WO2015/172746
PCT Pub. Date: Nov. 19, 2015

(65) Prior Publication Data
US 2017/0087170 A1    Mar. 30, 2017

Related U.S. Application Data

(60) Provisional application No. 61/994,486, filed on May 16, 2014.

(51) Int. Cl.
*A61K 31/704*    (2006.01)

(52) U.S. Cl.
CPC .................................. *A61K 31/704* (2013.01)

(58) Field of Classification Search
None
See application file for complete search history.

(56) References Cited

U.S. PATENT DOCUMENTS

| 8,080,568 B1 * | 12/2011 | Kim | C07D 471/04 |
| | | | 514/357 |
| 9,844,560 B2 * | 12/2017 | Lee | A61K 31/704 |
| 10,172,876 B2 * | 1/2019 | Lee | A61K 45/06 |

FOREIGN PATENT DOCUMENTS

WO    WO-2005102326 A2 *  11/2005  ........... A61K 31/404

* cited by examiner

*Primary Examiner* — Traviss C McIntosh, III
(74) *Attorney, Agent, or Firm* — WPAT, PC

(57) ABSTRACT

The present invention provides a method of inhibiting renal fibrosis in a subject in need thereof.

5 Claims, 12 Drawing Sheets

A

B

A

B

A

B

A

B

C
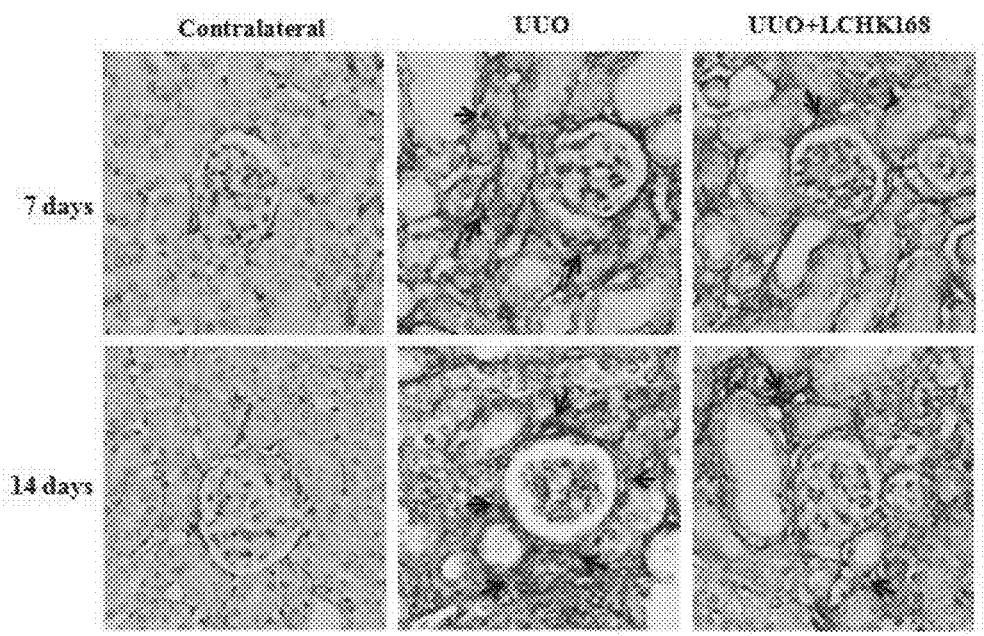
D
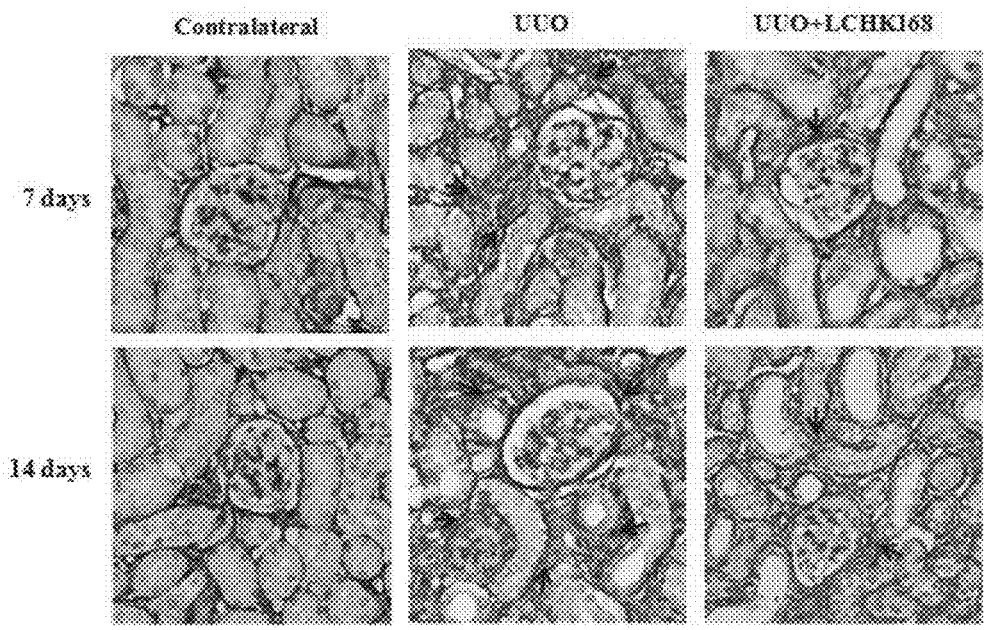
Fig. 4 (Cont')

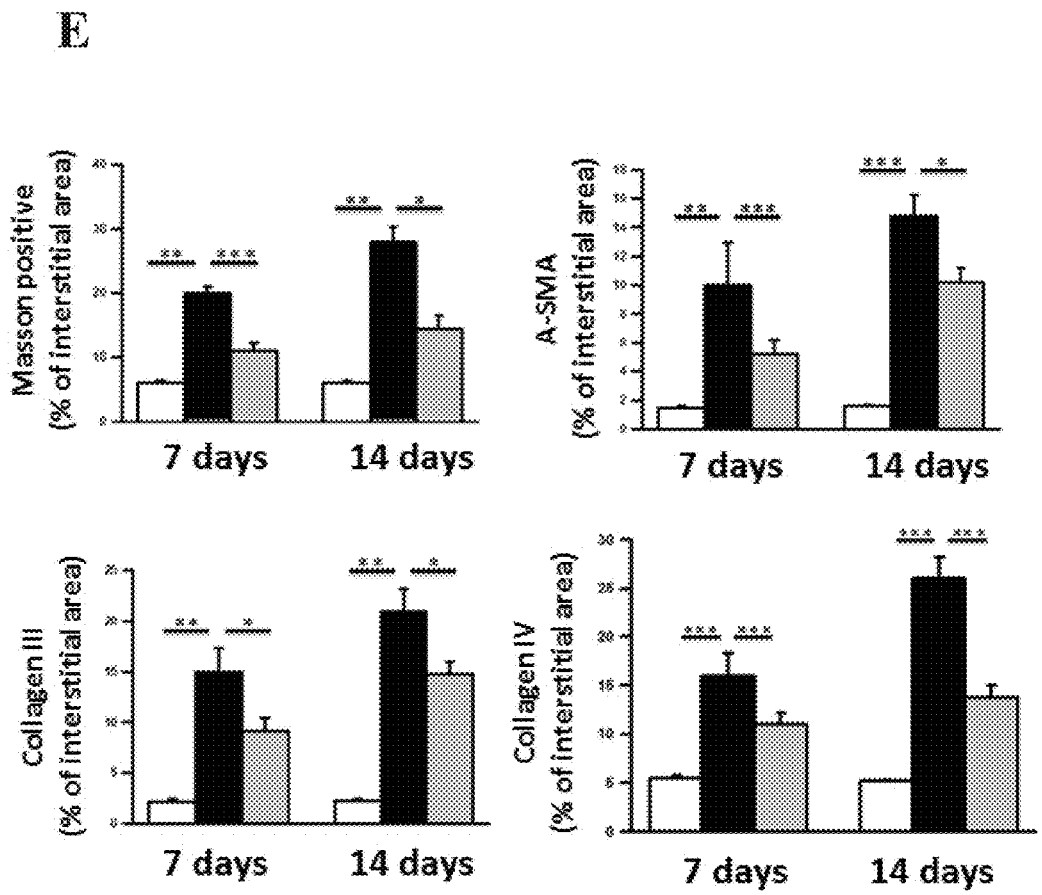
Fig. 4 (Cont')

A

B

A

B

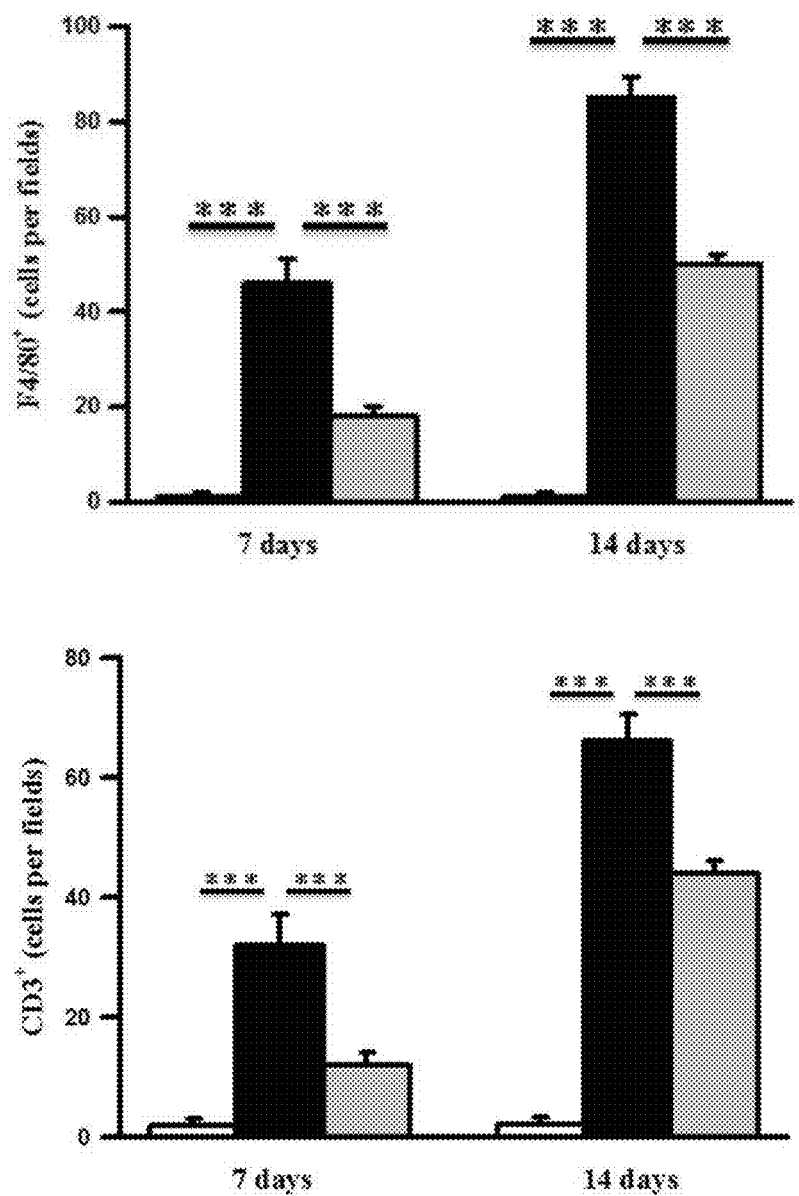
Fig. 6 (Cont')

A

B

C

A

B

A

B

USE OF GINSENOSIDE M1 FOR INHIBITING RENAL FIBROSIS

FIELD OF THE INVENTION

The present invention relates to a new use of ginsenoside M1 for inhibiting renal fibrosis, particularly interstitial fibrosis.

BACKGROUND OF THE INVENTION

Renal fibrosis is the final stage of renal diseases. The causes of renal fibrosis include ureteral obstruction.

Ureteral obstruction is one of the most common problems confronting the urologist. Ureteral obstruction causes impedance to the flow of urine in the ureter. Most commonly, obstruction occurs at the ureteropelvic junction. The broader term "obstructive uropathy" can be used to indicate any obstruction to urinary flow occurring between the renal pelvis and the urethra, which causes a developing hydronephrosis and associated renal impairment. Urethral strictures and benign prostatic hypertrophy are cases in point. The incidence of unilateral ureteric obstruction (UUO) is reported as 1/1,000 in adults. Ureteric calculi are the most common cause, and acute obstruction typically presents with significant renal colic as the major symptom. See, for example, Docherty et al., evidence that inhibition of tubular cell apoptosis protects against renal damage and development of fibrosis following ureteric obstruction, Am J Physiol Renal Physiol. 2006 January; 290 (1):F4-13.

In the beginning of UUO, the interstitium is infiltrated by monocytes, which are 'classically' activated to macrophages that release cytokines such as TGF-β1 and tumor necrosis factor-α (TNF-α). In turn, TGF-β1 promotes a phenotypic response of tubular epithelial cells either to undergo apoptosis (leading to tubular atrophy) or to undergo epithelial-mesenchymal transition (EMT), becoming fibroblasts that migrate to the interstitium. Angiotensin II (ANG II), produced by the activation of monocytes, stimulates the production of nuclear factor-κB (NF-κB), which leads to the recruitment of more macrophages, as well as to the production of reactive oxygen species (ROS), which aggravates renal tubular injury. In contrast, alternatively activated macrophages can enhance tubular cell survival and proliferation. Endothelial cells can undergo endothelial-mesenchymal transition (EndMT) or apoptosis, which leads to capillary loss and secondary renal ischemia and hypoxia. Resident pericytes and infiltrating hematopoietic stem cells can also differentiate into fibroblasts. Under the stimulus of cytokines, such as TGF-β1 produced by macrophages or other cells, fibroblasts synthesize stress fibers and undergo further differentiation to become myofibroblasts. The myofibroblasts are contractile and augment the deposition of the extracellular matrix (ECM), leading to progressive interstitial fibrosis. This process finally leads to progressive renal fibrosis and irreversible renal failure. See, for example, Chevalier et al., Ureteral obstruction as a model of renal interstitial fibrosis and obstructive nephropathy, Kidney Int. 2009 June; 75 (11):1145-52.

Ginsenosides, the main active ingredients of ginseng, are known to have a variety of pharmacological activities, e.g. antitumor, antidiabetic, antifatigue, antiallergic and antioxidant activities. Ginsenosides share a basic structure, composed of gonane steroid nucleus having 17 carbon atoms arranged in four rings. Ginsenosides are metalized in the body, and a number of recent studies suggest that ginsenoside metabolites, rather than naturally occurring ginsenosides, are readily absorbed in the body and act as the active components. Among them, ginsenoside M1 is known as one metabolite of protopanaxadiol-type ginsenosides via the gypenoside pathway by human gut bacteria. Until now, no prior art references report the effect of ginsenoside M1 in treatment of renal fibrosis.

BRIEF SUMMARY OF THE INVENTION

In the present invention, it is unexpected found that ginsenoside M1 is effective in inhibiting renal fibrosis. Therefore, the present invention provides a new approach for treatment or prevention of renal fibrosis in a subject.

In particular, the present invention provides a method for inhibiting renal fibrosis in a subject in need thereof comprising administering an effective amount of ginsenoside M1 to the subject.

In some embodiments, the subject is a patient with an obstructive nephropathy.

In some embodiments, the method of the invention is effective in reducing or alleviating one or more symptoms or conditions, including but not limited to, mononuclear leukocyte inflammation, tubular dilation, tubular atrophy, proliferation of tubular epithelial cells, activation of fibroblast or myofibroblast and deposition of collagens (e.g. III or IV), particularly in the tubulointerstitial compartment of the subject.

In some embodiments, the method of the invention is effective in reducing or alleviating mononuclear leukocyte infiltration or fibrosis in renal interstitial in the subject.

In some embodiments, the ginsenoside M1 is administered by parenteral or enteral route.

In some embodiments, the ginsenoside M1 is administered prior to or at the time of occurrence of renal fibrosis.

In some embodiments, the ginsenoside M1 is administered after occurrence of renal fibrosis.

Also provided is use of ginsenoside M1 for manufacturing a medicament for treating renal fibrosis.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments. It should be understood, however, that the invention is not limited to the preferred embodiments shown. In the drawings.

DETAILED DESCRIPTION OF THE INVENTION

Figure 1:
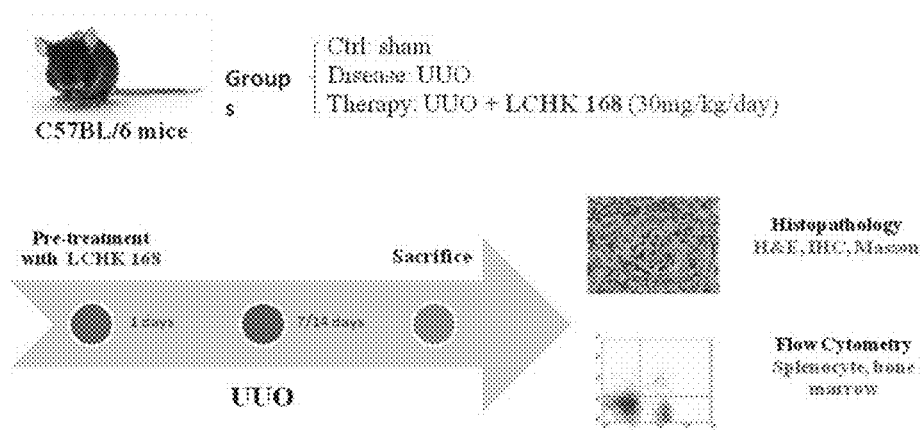
FIG. 1 shows the establishment of the UUO animal model, including (A) the experimental procedure, (B) the surgical procedure of the UUO animal model wherein the left is the diseased kidney after ligation of ureter and the right is the normal kidney without ligation of ureter.
Figure 1:
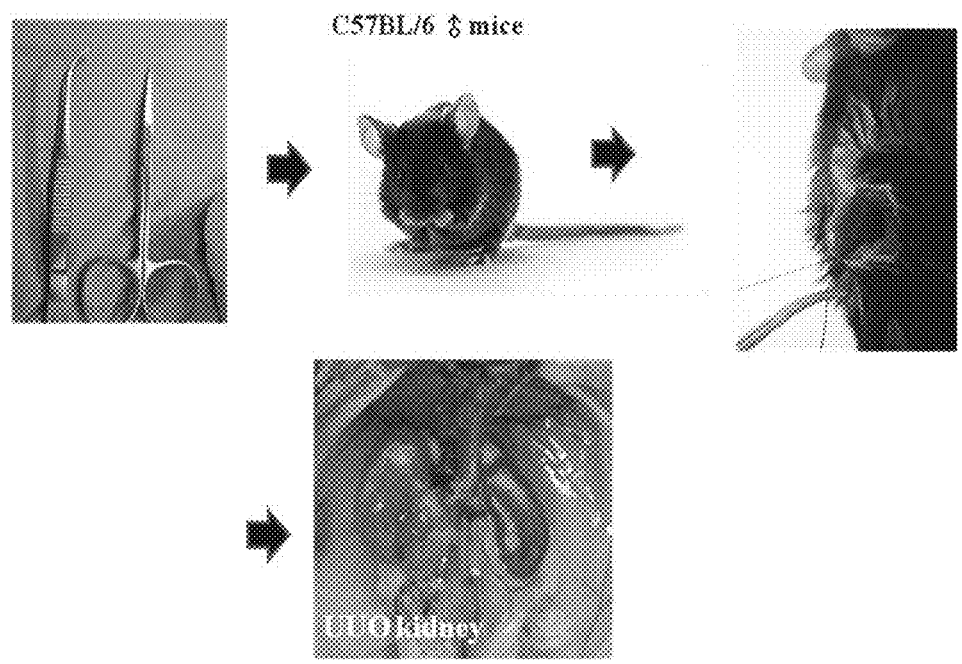

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

In the present invention, it is unexpectedly found that ginsenoside M1 is effective in inhibiting renal fibrosis. In particular, it is found that in the mice UUO model, the renal damage/inflammation is reduced and the progression to renal fibrosis is inhibited or alleviated.

The surgical-intervented UUO model on rodents has been used for decades as a high-throughput experimental model for UUO. This model is not complicated by hypertension, proteinuria or hyperlipidemia, and does not involve any apparent immune or toxic renal insult. Depending on the duration of obstruction, UUO can mimic various stages of obstructive nephropathy that ultimately lead to tubulointerstitial fibrosis. The animal's lifespan is not compromised, because the function of the contralateral kidney is maintained or even increased as a result of compensatory functional and anatomic hypertrophy. Other Advantages of this model include the fact that the progression of renal fibrosis is highly predictable and reproducible and leads to significant fibrosis and nephron loss in a relatively short period (7-14 days). See, for example, Eddy et al., Investigating mechanisms of chronic kidney disease in mouse models, Pediatr Nephrol. 2012 August; 27 (8):1233-47; and Grande M T and López-Novoa J M, Fibroblast activation and myofibroblast generation in obstructive nephropathy, Nat Rev Nephrol. 2009 June; 5 (6):319-28.

The examples and data below show the unexpected effects of ginsenoside M1, including (1) a reduction in cell apoptosis and tubular damage in renal interstitial tissues (2) prevention of fibrosis and collage deposition in renal interstitial tissues, (3) a reduction of NF-κB activation, (4) prevention of macrophage and T cell infiltration of the kidney, and (5) maintenance of normal function of hematopoietic stem cell and systemic cellular immunity.

Accordingly, the present invention provides a new approach for inhibition of renal fibrosis in a subject in need by administering an effective amount of ginsenoside M1 to the subject.

Ginsenoside M1, 20-O-β-D-glucopyranosyl-20(S)-protopanaxadiol, is one of saponin metabolites known in the art. The chemical structure of ginsenoside M1 is as follows:

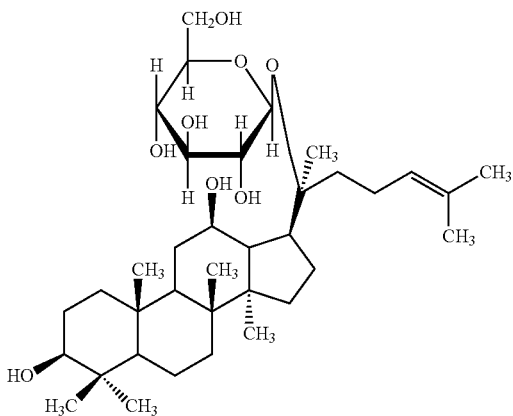

Ginsenoside M1 is known as one metabolite of protopanaxadiol-type ginsenosides via the gypenoside pathway by human gut bacteria. Ginsenoside M1 can be found in blood or urine after intake. Ginsenoside M1 may be prepared from ginseng plants through fungi fermentation by methods known in the art, such as Taiwan Patent Application No. 094116005 (I280982) and U.S. Pat. No. 7,932,057, the entire content of which is incorporated herein by reference. In certain embodiments, the ginseng plants for preparing the ginsenoside M1 include Araliaceae family, Panax genus, e.g. P. ginseng and P. pseudo-ginseng (also named Sanqi). In general, the method of preparation of ginsenoside M1 includes the steps of (a) providing powder of ginseng plant materials (e.g. leaves or stems); (b) providing a fungus for fermenting the ginseng plant materials, wherein the fermentation temperature is ranged from 20-50° C., the fermentation humidity is ranged from 70-100%, the pH value is ranged from 4.0-6.0, and the fermentation period is ranged from 5-15 days; (c) extracting and collecting the fermentation products; and (d) isolating 20-O-β-D-glucopyranosyl-20(S)-protopanaxadiol from the fermentation products.

When ginsenoside M1 is described as "isolated" or "purified" in the present invention, it should be understood as not absolutely isolated or purified, but relatively isolated or purified. For example, purified ginsenoside M1 refers to one that is more purified compared to its naturally existing form. In one embodiment, a preparation comprising purified ginsenoside M1 may comprise ginsenoside M1 in an amount of more than 50%, more than 60%, more than 70%, more than 80%, more than 90%, or 100% (w/w) of the total preparation. It should be understood that when a certain number was used herein to show a ratio or dosage, said number generally includes that within the range of 10% more and less, or more specifically, the scope of 5% more and less than the number.

The present invention provides a method for inhibiting renal fibrosis comprising administering an effective amount of ginsenoside M1 to a subject in need thereof. Also provided is use of ginsenoside M1 for manufacturing a medicament for inhibiting renal fibrosis in a subject in need thereof. The medicament of the invention is effective in reducing or alleviating one or more symptoms or conditions, including but not limited to, mononuclear leukocyte inflammation, tubular dilation, tubular atrophy, proliferation of tubular epithelial cells, activation of fibroblast or myofibroblast and deposition of collagens (e.g. III or IV), particularly in the tubulointerstitial compartment of the subject. Specifically, the medicament of the invention is effective in reducing or alleviating mononuclear leukocyte infiltration or fibrosis in renal interstitial in the subject.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like). In certain embodiments, the subject to be treated by the method of the invention is identified as having obstructive nephropathy.

The term "treating" or "treatment" as used herein refers to the application or administration of a composition including one or more active agents to a subject afflicted with a disorder, a symptom or condition of the disorder, or a progression of the disorder, with the purpose to cure, heal, alleviate, relieve, alter, remedy, ameliorate, improve, or affect the disorder, the symptom or condition of the disorder, the disabilities induced by the disorder, or the progression of the disorder or the symptom or condition thereof. The term "preventing" or "prevention" as used herein refers to application or administration of a composition including one or more active agents to a subject who is susceptible or predisposed to a disorder or a symptom or condition thereof and thus relates to prevention of the occurrence of the disorder or the symptom or condition thereof or underlying causes thereof.

The term "effective amount" used herein refers to the amount of an active ingredient to confer a desired therapeutic effect in a treated subject. For example, an effective amount for treating or preventing renal fibrosis can be an amount that can prohibit, improve, alleviate, reduce or prevent one or more symptoms or conditions or progression thereof such as mononuclear leukocyte inflammation, tubular dilation, tubular atrophy, proliferation of tubular epithelial cells, activation of fibroblast or myofibroblast and deposition of collages (III or IV), particularly in the tubulointerstitial compartment. The symptoms may be determined and evaluated using methods known in the art based on various disease progress-related indexes, for example by analyzing renal sections via staining. The effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of ginsenoside M1 used in the present invention is 10 to 1,000 mg/kg daily. In some examples, the oral dosage of ginsenoside M1 used in the present invention is 100 to 300 mg/kg daily, 50 to 150 mg/kg daily, 25 to 100 mg/kg daily, 10 to 50 mg/kg daily, or 5 to 30 mg/kg daily. In addition, in some embodiments of the invention, ginsenoside M1 is administered periodically for a certain period of time, for example, daily administration for at least 5 days, 10 days or 15 days, one month or two months or longer.

According to the present invention, ginsenoside M1 may be used as an active ingredient for treating or preventing renal fibrosis. In one embodiment, an effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, ginsenoside M1 or compositions comprising ginsenoside M1 as the active ingredient may be used in treating or preventing renal fibrosis. Specifically, ginsenoside M1 or compositions comprising ginsenoside M1 as the active ingredient may be administered to individuals with renal fibrosis or individuals with the risk of acquiring renal fibrosis so as to prevent occurrence of the disease or improve the symptoms or delay deterioration of the symptoms. Specifically, the ginsenoside M1 can be administered prior to or at the time of occurrence of renal fibrosis, or the ginsenoside M1 can be administered after occurrence of renal fibrosis.

In addition, according to the present invention, ginsenoside M1 or compositions comprising ginsenoside M1 as the active ingredient may be used in combination with existing therapeutic methods or medicaments, such as pharmaceutical treatment, including but not limited to corticosteroids (such as prednisolone), non-steriodal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors)). In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

The present invention is further illustrated by the following examples, which are provided for the purpose of demonstration rather than limitation.

Example

1. Materials and Methods 1.1 Animal Model and Experimental Protocol

UUO (Unilateral Ureteral Obstruction) Animal Model

Male 8-week-old C57BL/6 mice were purchased form National Laboratory Animal Breeding and Research Center (Taipei, Taiwan) and maintained at the animal center of the National Defense Medical Center (Taipei, Taiwan). All animal experiments were performed with the approval of the Institutional Animal Care and Use Committee of The National Defense Medical Center, Taiwan, and were consistent with the National Institutes of Health Guide for the Care and Use of Laboratory Animals.

Mice were first anesthetized with sodium pentobarbital (50 mg/kg, i.p.). After a left flank incision was taken, the left ureter was exposed, ligated with 6-0 silk sutures at two points, and cut between the two ligatures. Lastly, the peritoneal membrane and skin were sutured. Sham surgery was performed as control by following all steps of UUO-procedure except ligation and cut of ureter. (Xiao et al. Adenosine A2A receptor: a target for regulating renal interstitial fibrosis in obstructive nephropathy, PLoS One. 2013 Apr. 9; 8 (4):e60173).

Briefly, all mice received preoperative analgesia (subcutaneous injection of 50 mg/kg buprenorphin (Temgesic, Shering-Plough)) and the right ureter was subsequently ligated with 6.0 silk through a small abdominal incision under 2.0% isoflurane-induced anesthesia. The abdomen was closed in two layers and mice were allowed to recover from surgery for 12 hours at 28° C. in a ventilated stove. Mice were sacrificed 7 or 14 days after surgery (Pulskens, et al. Nlrp3 prevents early renal interstitial edema and vascular permeability in unilateral ureteral obstruction, PLoS One. 2014 Jan. 15; 9 (1):e85775).

1.2 Ginsenoside M1 and Administration

Ginsenoside M1, 20-O-β-D-glucopyranosyl-20(S)-protopanaxadiol (named LCHK168 below), was prepared by methods known in the art, such as those described in Taiwan Patent Application No. 094116005 (I280982) and U.S. Pat. No. 7,932,057. LCHK168 was dissolved in 3% cremophore (Sigma-Aldrich). Starting from one day before UUO operation, mice were given a daily dose of LCHK168 (30 mg/kg) by intraperitoneal injection till sacrifice.

1.3 Renal Histopathology

Paraffin-embedded kidney tissues were sectioned and stained with Masson's trichrome and hematoxylin and eosin (H&E) using standard protocols. For histopathology, the tissues were fixed in 10% buffered formalin and embedded in paraffin, and then sections (3 μm) were prepared and stained with hematoxylin and eosin (H&E).

Sections all are examed after mounting. The methods of semi-quantitative analysis are according to the degree of inflammation and fibrosis on renal tubulointerstitial whereas and randomly selected 20 fields randomly for scoring. "0" indicates normal morphology, "1" indicates influent area is less than 10%, "2" indicates influent area is around 10 to 30%, "3" indicates influent area is around 30 to 50%, and "4" indicates influent area is more than 50%.

1.4 Immunohistochemistry (IHC) and Detection of Apoptosis

For IHC, formalin-fixed and paraffin-embedded tissue sections were incubated overnight at 4° C. with anti-bodies against PCNA (Santa Cruz Biotechnology, Santa Cruz, Calif., USA), CD3 (DAKO, Glostrup, Denmark), α-SMA (Thermo Fisher Scientific, Waltham, Mass., USA), Collagen III, Collagen IV (both from SouthernBiotech, Birmingham, Ala., USA), F4/80 (monocytes/macrophages; Serotec, Raleigh, N.C., USA), phospho-NF-κB p65 (pNF-κB p65; Cell Signaling Technology, Beverly, Mass., USA), diluted in DAKO antibody dilution buffer (DAKO, Glostrup, Denmark), and then for 1 h at room temperature with horseradish peroxidase (HRP)-conjugated second antibodies (DAKO) or anti-rabbit polymer-HRP (BioGenex, Fremont, Calif., USA) in the same buffer; then DAB (BioGenex) was added. Hematoxylin was used to counterstain nuclei. For detection of apoptosis, terminal deoxynucleotidyl transferase-mediated dUTP nick-end labeling (TUNEL) was used. Formalin-fixed tissue sections were stained using an ApopTag Plus Peroxidase In Situ Apoptosis detection kit (Chemicon, Temecula, Calif., USA) according to the manufacturer's instructions. The abundance of α-SMA, Collagen III, Collagen IV or the number of phosphorylated NF-κB p65$^+$, PCNA$^+$, F4/80$^+$, CD3$^+$ and apoptotic cells was counted at a magnification of ×400 randomly selected fields of the tubulointerstitial compartment in the cortical area by Pax-It quantitative image analysis software (Paxcam).

1.5 Flowcytometry

Splenocytes from the mice were treated with Tris-buffered ammonium chloride to eliminate erythrocytes, washed, and resuspended in RPMI1640 medium supplemented with 10% fetal calf serum, Hepes buffer, L-glutamine, and penicillin/streptomycin (all from Invitrogen/Life Technologies, Grand Island, N.Y., USA). The cells were then stained for surface markers of T or B cells, using FITC-conjugated anti-mouse CD3 antibodies (17A2) for T cells, anti-mouse CD19 antibodies (1D3) for B cells, and phycoerythrin-conjugated anti-mouse CD69 antibodies (H1.2F3; all antibodies from BD Biosciences). For bone marrow cells analysis, bone marrow from mice were isolated as described (Takeshita S et al., 2014), and were stained with antibodies against mouse Sca-1 (BD Biosciences) or CD34 (eBioscience, San Diego, Calif., USA). Flow cytometric analysis was carried out using a FACSCalibur (BD Biosciences).

1.6 Masson's Trichrome Staining

Three μm renal sections are incubated in 75° C. for 15 minutes. Transfer the slides above into xyline and gradient alcohol. Mordant is mounted onto slides following stain with hematoxylin for 1 minute. After staining with 0.75% orange G solution, masson stain solution B, 2.5% phosphotungostic acid solution, and aniline blue stain solution, slides are washed by 1% acetic acid twice and mount with gum Arabic. Air dry for few minutes and the stained sections are exam onto optical microscope.

1.7 Enzyme-linked Immunosorbent Assay

Urine samples are collected from calyx and pelvis by 29G insulin syringe. As normal control, urine is collected by metabolic cages. MCP-1, TNF-α, and IL-1β are then detected by ELISA following instruction manual (eBioscience and R&D). Briefly, capture antibody is coated in 96 well plates over night. After wash with PBST, blocking buffer, samples, detection antibody, avidin-HRP are loaded in order. Colors are developed after TMB substrate step, and then add 2N $H_2SO_4$ to stop reaction. Finally, O.D. 450 nm is measure.

1.8 Statistical Analysis

Values are means ±SD. Comparison between two groups was performed using Student's t-test. A P value <0.05 was considered statistically significant.

2. Results 2.1 Establishment of Experimental UUO Model

Experiments were performed on 8-10 weeks old C57BL/6 mice. Mice were randomly divided into sham control, disease control and LCHK168 therapy group and were sacrificed after UUO for 7 or 14 days. Retention of urine in the pelvis of UUO kidney was observed, indicated UUO model established successfully. See FIG. 1A and FIG. 1B.

2.2 Renal Histopathology Evaluation

Figure 2:
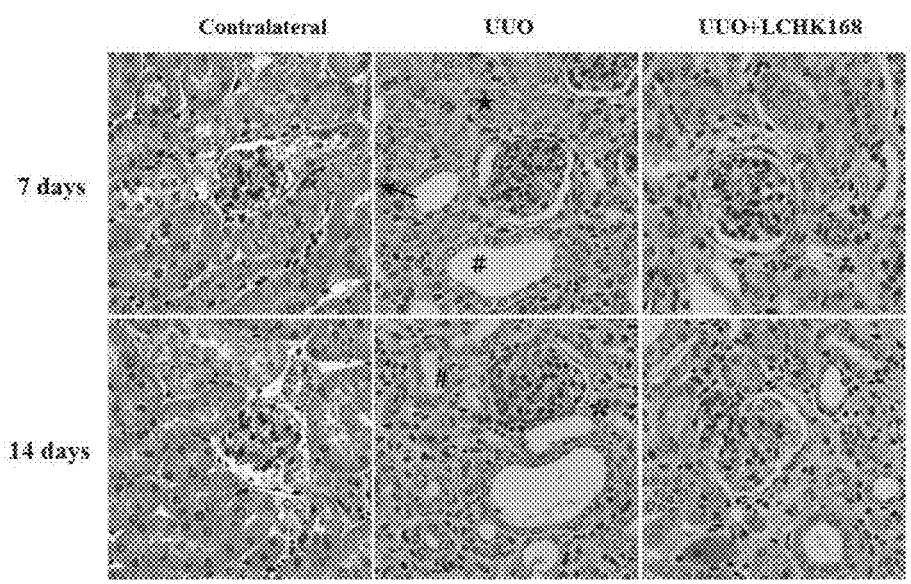
FIG. 2 shows the kidney histopathological evaluation by H&E staining wherein the arrows indicate dilated tubule. (A) H&E staining for renal histopathological evaluation. "#" indicates dilated renal tubule, asterisk indicates monocytes, and "*" indicates atrophic renal tubule. The original magnification was ×400 for histopathology. (B) Semi-quantitative shows tubulointerstitial injury scores (TIS). White, black and gray columns represent normal control mice, disease-control mice and LCHK168+UUO mice, respectively. ***p<0.005.
Figure 2:
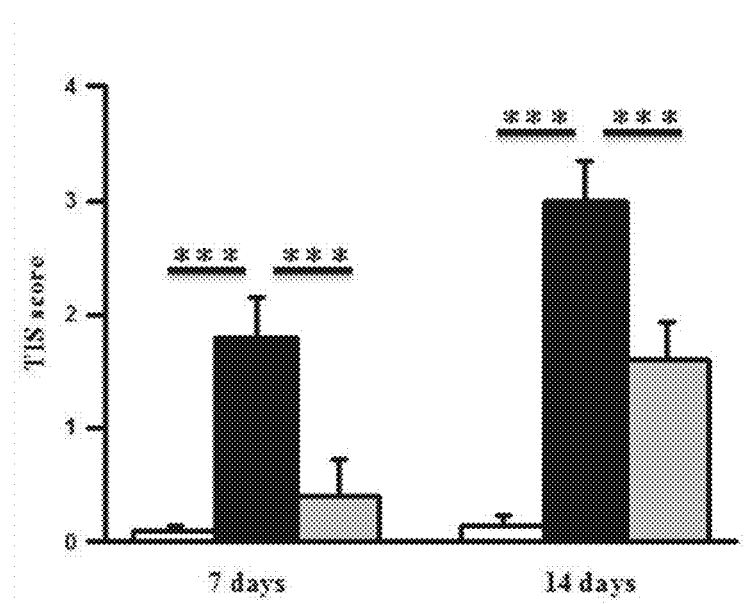

Renal tissues were collected, fixed and underwent H&E staining. As shown in FIG. 2, on 7 days of UUO, disease control mice showed significant mononuclear leukocyte infiltration and tubular dilation in the interstitial area, and this histopathology was inhibited by LCHK168 administration. On 14 days of UUO, fibrosis and tubular atrophy are observed, which are significantly inhibited after LCHK168 administration.

2.3 Renal Cell Apoptosis and Proliferation Evaluation

Figure 3:
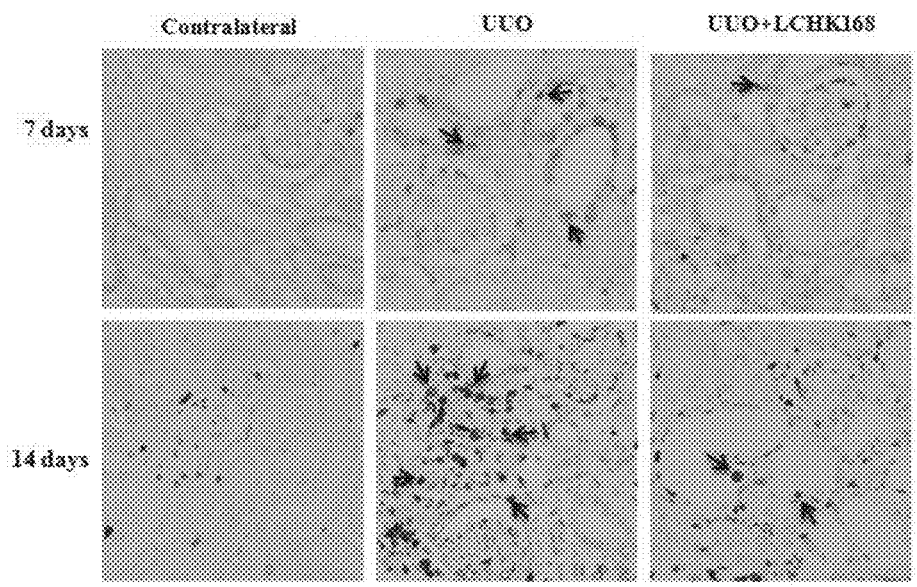
FIG. 3 shows renal cell apoptosis and proliferation evaluation, including (A) detection of PCNA by immunohistochemical staining wherein the arrows indicate positively stained cells, and (B) semi-quantitative results. Original magnification is ×400. White, black and gray columns represent normal control mice, disease-control mice and LCHK168+UUO mice, respectively. ***p<0.005.
Figure 3:
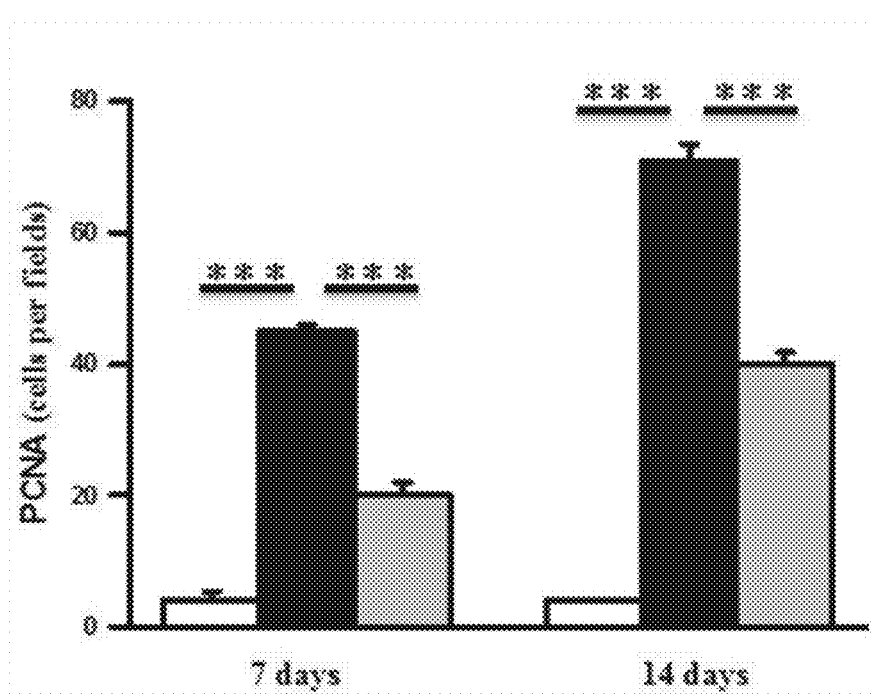

In the UUO kidney, mechanic stress caused by the retention of urine, and cytokine and ROS release by renal cells as a response to the stress will cause damage to cells, which lead to cell self-renew or apoptosis reaction. TUNNEL staining of renal section for apoptotic cells showed the UUO renal interstitial area, and was decrease after LCHK168 administration. See FIG. 3A.

Immunohistochemical staining of renal section with proliferating cell nuclear antigen (PCNA), a marker not only for the proliferative status of tubular epithelial cells but also activated myofibroblast and inflammatory cells, showed significant increased after UUO, particularly in dilated tubule. However, PCNA expression was decrease after administration of LCHK168. These results indicated LCHK168 might attenuated cell apoptosis and damage. See FIG. 3B.

2.4 Fibrosis Expression Evaluation

Figure 4:
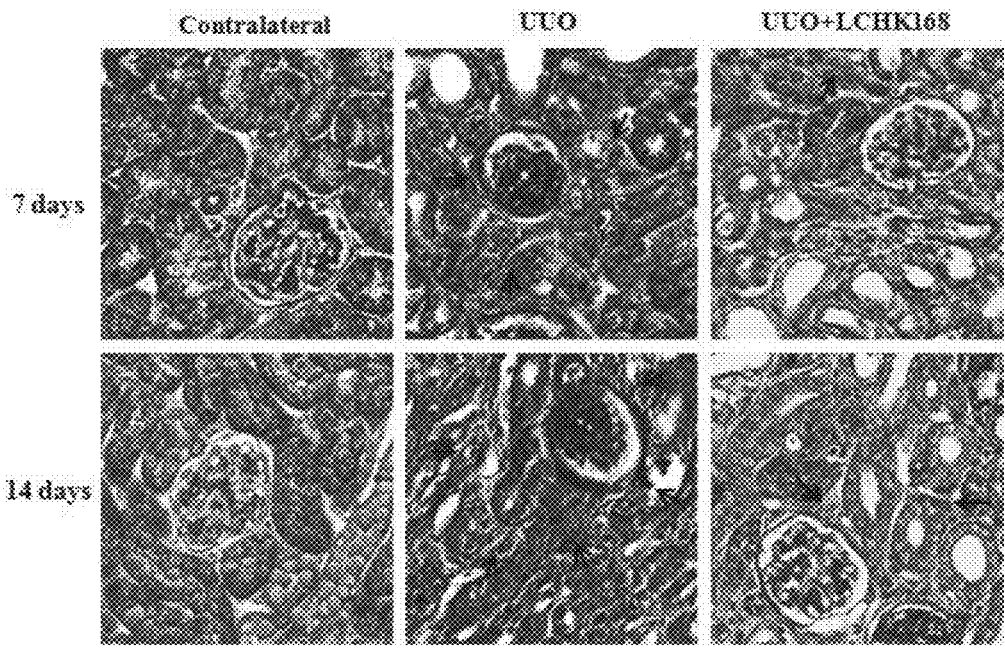
FIG. 4 shows fibrosis expression evaluation, including (A) expression of fibrotic collagens in renal tissues by Masson's trichome staining, (B) expression of smooth muscle α-actin (α-SMA) in renal tissues by immunohistochemical staining, (C) expression of collagen III in renal tissues by immunohistochemical staining, (D) expression of collagen IV in renal tissues by immunohistochemical staining, wherein the arrows indicate positively stained cells, and (E) semi-quantitative results. Original magnification is ×400. White, black and gray columns represent normal control mice, disease-control mice and LCHK168+UUO mice, respectively. *p<0.05, p<0.01, *p<0.005.
Figure 4:
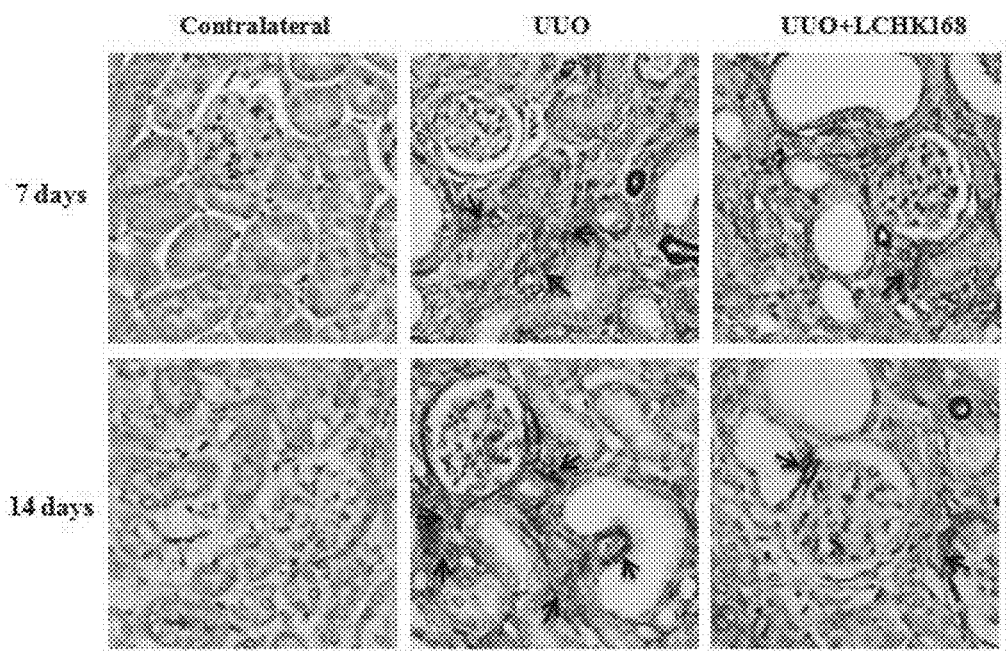

In UUO kidney, fibrosis is a maladaptive response to renal tissue damage and will develop to irreversible renal dysfunction if obstruction persisted. Histochemical staining of renal section with Masson's trichrom staining showed a significant increase of fibrosis tissue in the UUO interstitial area compared to sham control, and was decreased after LCHK168 administration. See FIG. 4A. Further examination were performed by immunohistochemical staining of renal section for α-SMA, collagen III and IV, which strongly expressed in UUO interstitial area and decreased after LCHK168 administration. See FIG. 4B-E. These data obtained showed that LCHK168 might ameliorates myofibroblasts activation and renal fibrosis in renal interstitial.

Figure 5:
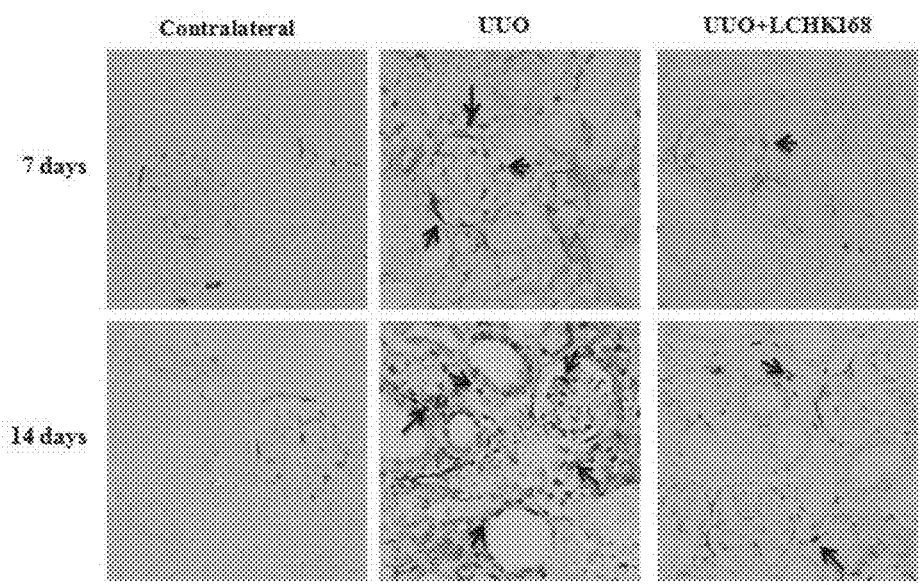
FIG. 5 shows (A) expression of NF-κB in renal tissues by immunohistochemical staining, wherein the arrows indicate positively stained cells, and (B) semi-quantitative results. Original magnification is ×400. White, black and gray columns represent normal control mice, disease-control mice and LCHK168+UUO mice, respectively. ***p<0.005.
Figure 5:
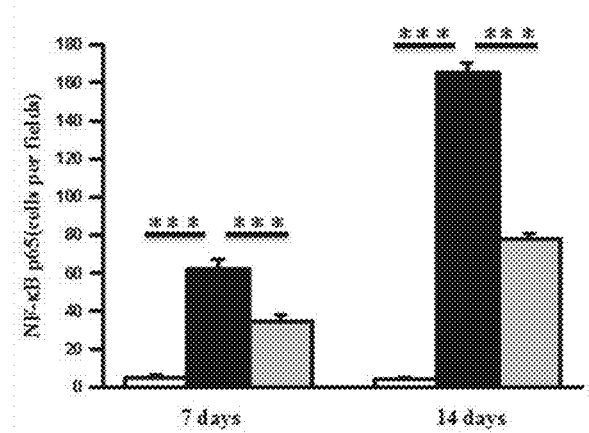

2.5 NF-κB Modulated Inflammatory Response 2.5.1 Expression of NF-κB in Renal Tissue NF-κB is an essential nuclear transcript factor for the modulation of inflammatory related factors for its stimulation of cytokine and cell-adhesion molecules. Previous studies indicated the expression level of NF-κB elevates in various inflammatory disorders, including kidney diseases Immunohistochemical staining of renal section for NF-κB showed an increase of NF-κB expression, and was inhibited after LCHK168 administration. See FIG. 5. This data showed LCHK168 may inhibit NF-κB in UUO kidney.

2.5.2 Mononuclear Leukocyte Infiltration

Figure 6:
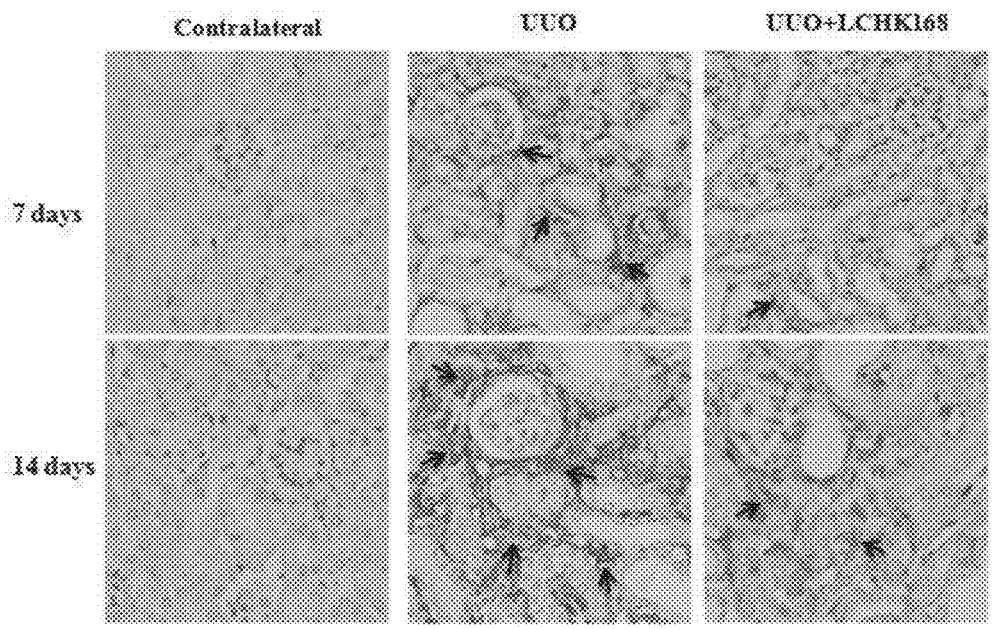
FIG. 6 shows mononuclear leukocyte infiltration in renal tissues, including detection of (A) F4/80$^+$ monocytes/macrophages and (B) CD3$^+$ T cells by immunohistochemical staining, wherein the arrows indicate positively stained cells, and (C) semi-quantitative results. Original magnification is ×400. White, black and gray columns represent normal control mice, disease-control mice and LCHK168+UUO mice, respectively. ***p<0.005.
Figure 6:
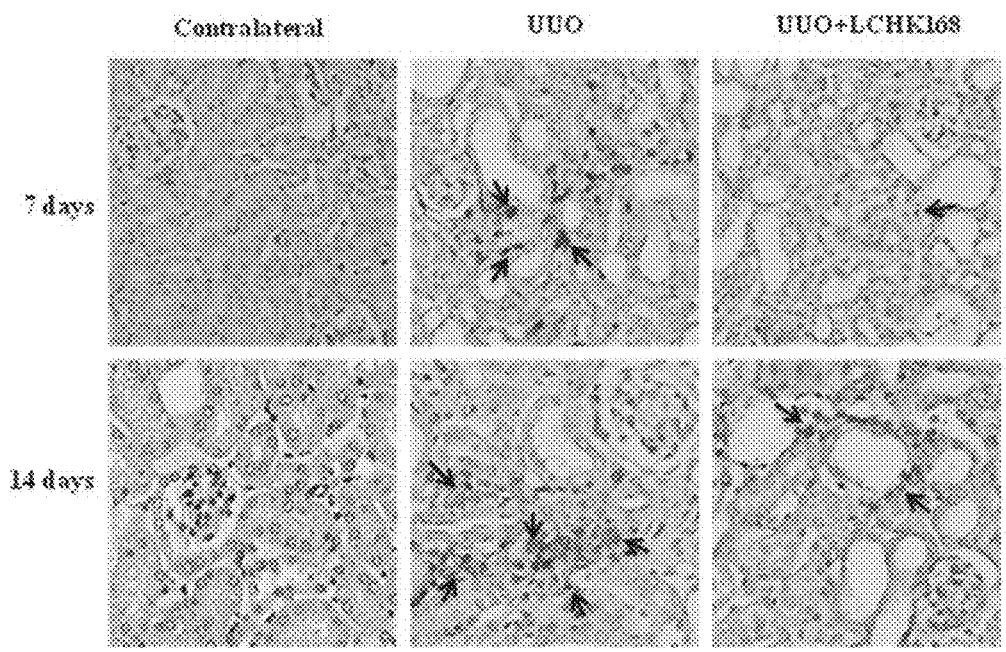
Figure 7:
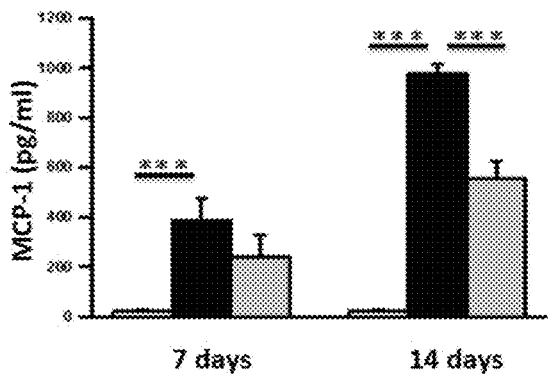
FIG. 7 shows that LCHK168 inhibits the expression level of MCP-1, TNF-α and IL-1β in pelvis urine. (A) MCP-1, (B) TNF-α, and (C) IL-1β are detected in urine samples by ELISA. White, black and gray columns represent normal control mice, disease-control mice and LCHK168+UUO mice, respectively. *p<0.05, p<0.01, *p<0.005.
Figure 7:
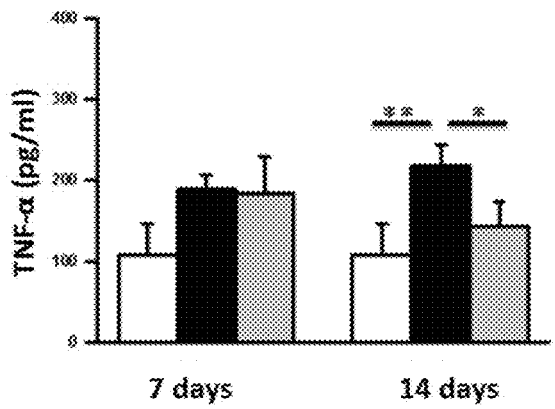
Figure 7:
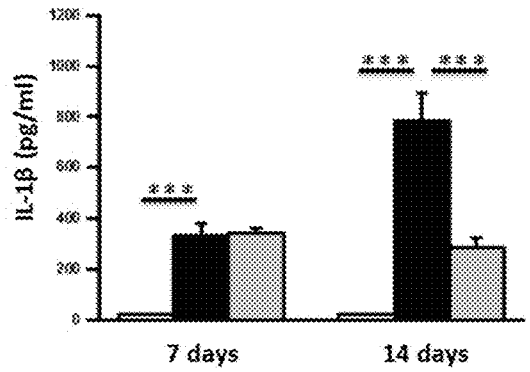

Previous studies indicated that inflammatory cells play an important role in the pathogenesis of UUO. Infiltration of mononuclear leukocyte, especially macrophage and T lymphocyte, can be observed in the early stage of UUO. With the persistent of obstruction, the activated inflammatory cells stimulate tubular epithelial cells or other inflammatory cells to release various cytokines and chemokines, cause more inflammatory cells recruiting to the renal interstitial area and induced renal inflammation and fibrosis. Evaluation of mononuclear leukocyte infiltration was carried out by immunohistochemical staining of renal section for F4/80 and CD3+, which are the markers for macrophage and T cells. The expression of F4/80 and CD3+ increased on after UUO and were decreased after LCHK168 administration. See FIGS. 6A, 6B. The data obtained showed LCHK168 might prevents macrophage and T cells infiltration in renal interstitial.

2.5.3 Evaluation of Expression of MCP-1, TNF-α and IL-1β in Urine

At initial stage, cytokine and chemokines are release focally in renal and could recruit immune cells. And the recruited immune cells then release more and more inflammatory factors. MCP-1, TNF-α, and IL-1β in renal pelvis are detected. Both UUO and UUO+LCHK group express higher MCP-1, TNF-α, and IL-1β compare to normal control group at day 7. Although the level of these cytokine and chemokines are significant decreased at day 14 on UUO+LCHK group compare to UUO group. The figure shows: LCHK168 could significant reduce urine MCP-1, TNF-α, and IL-1β level.

Figure 8:
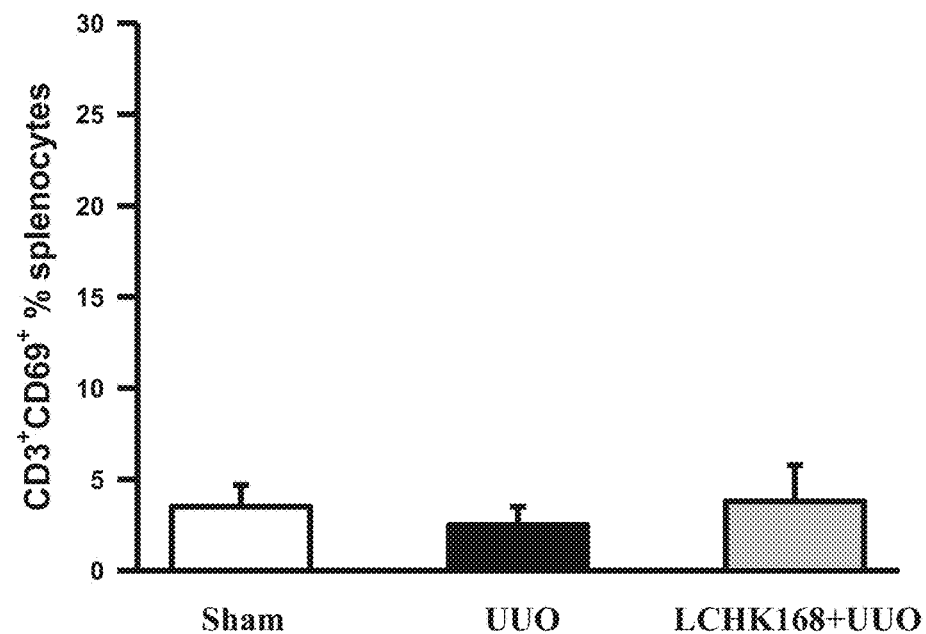
FIG. 8 shows evaluation for activation of cellular immunity, including detection of (A) CD3$^+$ CD69$^+$ T cells and (B) CD19$^+$ CD69$^+$ T cells by flow cytometry. White, black and gray columns represent normal control mice, disease-control mice and LCHK168+UUO mice, respectively.
Figure 8:
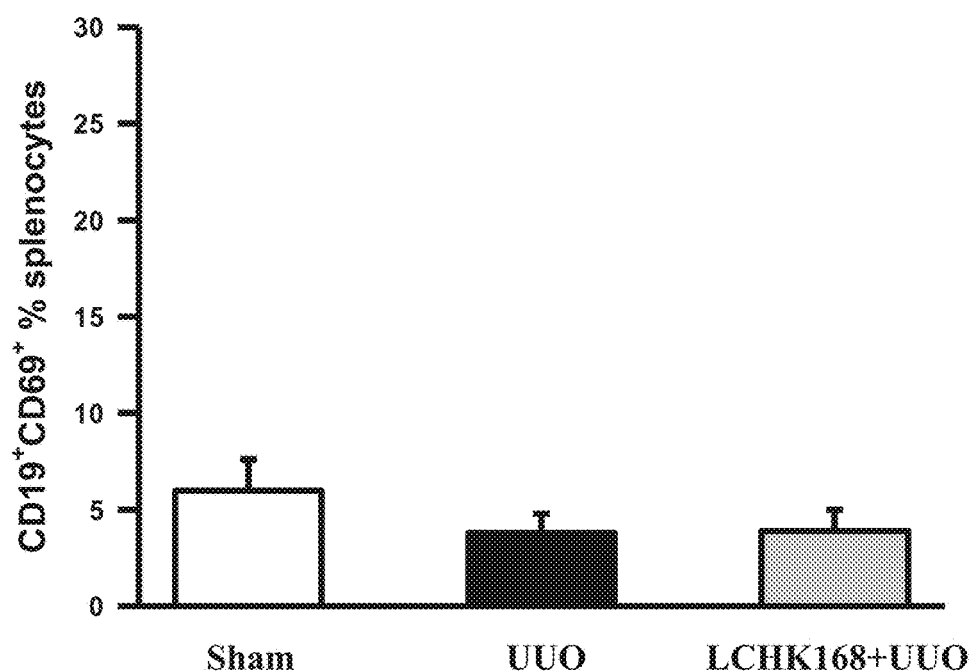

2.6 Activation of Cellular Immunity and Hematopoietic Stem Cell Activation 2.6.1 Activation of B and T Lymphocyte To examine LCHK168 whether prevents local inflammation and fibrosis through inhibition of systemic cellular immunity, we examined B cells and T cells activation in splenocytes by flow cytometry. As shown in FIGS. 8A and 8B, there was no significant change in the percentage of $CD3^+CD69^+$ (activated pan B) within three groups, nor was $CD19^+CD69^+$ (activated pan T). The data obtained indicated nephropathy caused by UUO might have little effect on systemic cellular immunity, and LCHK168 may not prevent local inflammation and fibrosis through inhibition of systemic cellular immunity.

2.6.2 Activation of Hematopoietic Stem Cell

Figure 9:
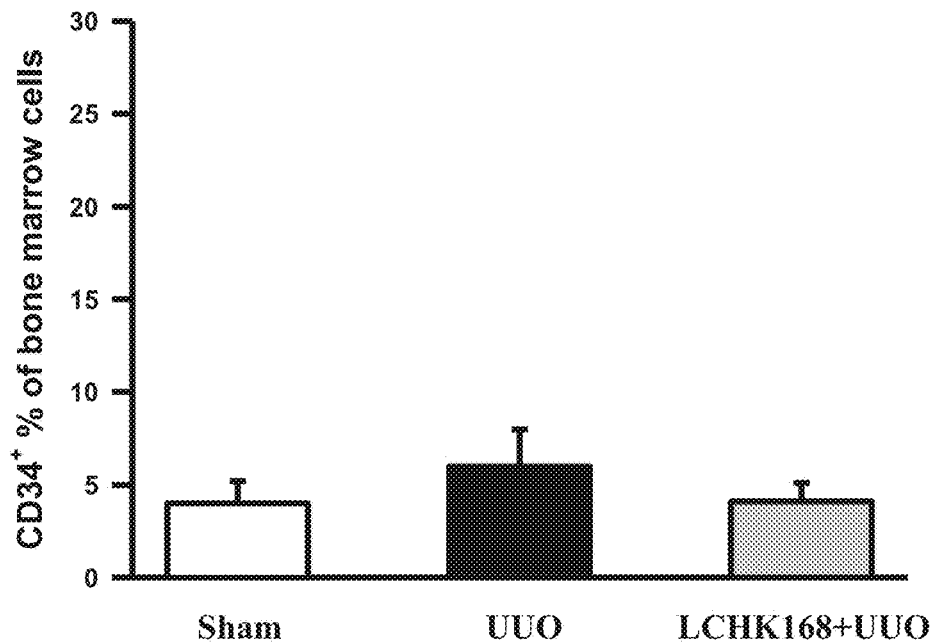
FIG. 9 shows evaluation of activation of hematopoietic stem cells, including detection of (A) CD34$^+$ stem cells and (B) Sca-1$^+$ hematopoietic stem cells by flow cytometry. White, black and gray columns represent normal control mice, disease-control mice and LCHK168+UUO mice, respectively.
Figure 9:
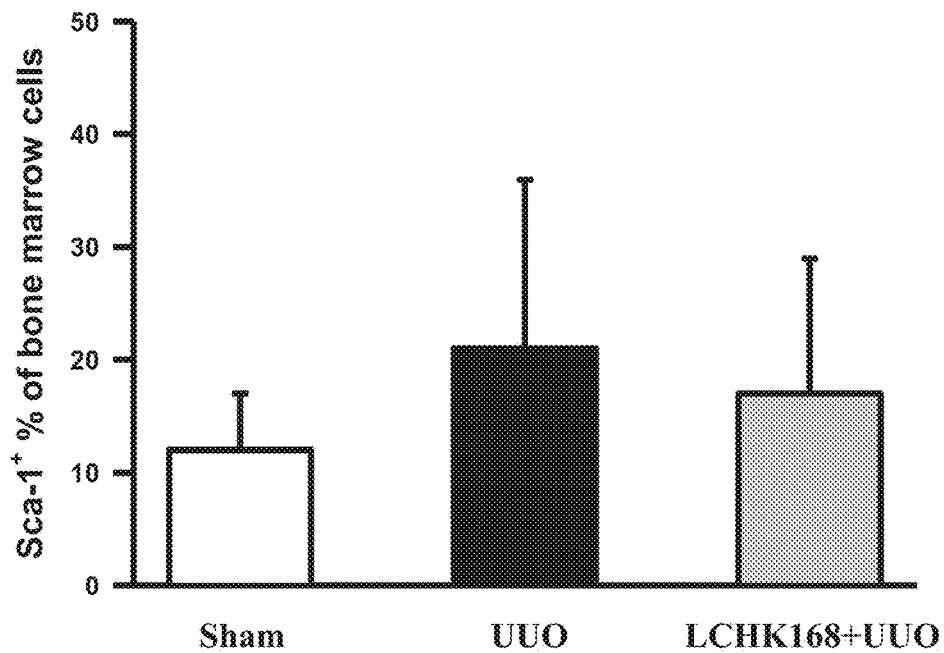

To examine LCHK168 whether prevents local inflammation and fibrosis through inhibition of hematopoietic stem cell activation, we examined stem cells and hematopoietic stem cell activation in bone marrow cells by flow cytometry. As shown in FIGS. 9A and 9B, there was no significant change in the percentage of Stem-cell antigen-1-positive cells (hematopoietic stem cell) and $CD34^+$ (stem cell) cells within three groups. The data obtained indicated nephropathy caused by UUO might have little effect on hematopoietic stem cell activity, and LCHK168 may not prevent local inflammation and fibrosis through inhibition of hematopoietic stem cell activity.

In summary, our study shows that ginsenoside M1 is effective in preventing development of renal fibrosis in the UUO model. In particular, the results shows (1) a reduction in cell apoptosis and tubular damage in renal interstitial tissues (2) prevention of fibrosis and collage deposition in renal interstitial tissues, (3) a reduction of NF-κB activation, (4) prevention of macrophage and T cell infiltration of the kidney, and (5) normal function of hematopoietic stem cell and systemic cellular immunity. All these findings suggest that ginsenoside M can be further developed to a candidate new drug for treatment or prevention of renal fibrosis.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

We claim:

1. A method of inhibiting renal fibrosis in a subject in need thereof comprising administering an effective amount of ginsenoside M1 to the subject.

2. The method of claim 1, wherein the subject is a patient with an obstructive nephropathy.

3. The method of claim 1, wherein the ginsenoside M1 is administrated in an amount effective in reducing or alleviating one or more symptoms or conditions, selected from the group consisting of mononuclear leukocyte inflammation, tubular dilation, tubular atrophy, proliferation of tubular epithelial cells, activation of fibroblast or myofibroblast and deposition of collagens, in the subject.

4. The method of claim 1, wherein the ginsenoside M1 is administrated in an amount effective in reducing or alleviating mononuclear leukocyte infiltration or fibrosis in renal interstitial in the subject.

5. The method of claim 1, comprising diagnosing or identifying the subject with an obstructive nephropathy prior to administration of ginsenoside M1.

* * * * *